US009763615B2

(12) United States Patent
Xu (10) Patent No.: US 9,763,615 B2
(45) Date of Patent: Sep. 19, 2017

(54) DEVICE AND METHOD FOR MONITORING BLADDER VOLUME OF A SUBJECT (71) Applicant: KONINKLIJKE PHILIPS N.V., Eindhoven (NL)

(72) Inventor: Jingping Xu, Shanghai (CN)

(73) Assignee: KONINKLIJKE PHILIPS N.V., Eindhvoen (NL)

( * ) Notice: Subject to any disclaimer, the term of this patent is extended or adjusted under 35 U.S.C. 154(b) by 0 days.

(21) Appl. No.: 15/039,900

(22) PCT Filed: Jan. 28, 2015

(86) PCT No.: PCT/EP2015/051743
§ 371 (c)(1),
(2) Date: May 27, 2016

(87) PCT Pub. No.: WO2015/114027
PCT Pub. Date: Aug. 6, 2015

(65) Prior Publication Data
US 2017/0000401 A1    Jan. 5, 2017

(30) Foreign Application Priority Data

Jan. 28, 2014  (WO) ............... PCT/CN2014/071668
May 15, 2014   (EP) .................................. 14168412

(51) Int. Cl.
A61B 5/20     (2006.01)
A61B 8/08     (2006.01)
(Continued)

(52) U.S. Cl.
CPC .............. A61B 5/204 (2013.01); A61B 5/746
(2013.01); A61B 8/08 (2013.01); A61B 8/4444
(2013.01);
(Continued)

(58) Field of Classification Search
CPC ........... A61B 5/204; A61B 5/746; A61B 8/08;
A61B 8/4444; A61B 8/4494; A61B
8/5233; A61B 8/5276; A61B 8/54; A61B
8/56
See application file for complete search history.

(56) References Cited

U.S. PATENT DOCUMENTS 6,372,951 B1    4/2002  Ter-Ovanesyan et al.
2006/0281992 A1  12/2006 Stothers et al.
(Continued)

FOREIGN PATENT DOCUMENTS

CN  101919705 A  12/2010
JP  2002306484 A  10/2002
(Continued)

OTHER PUBLICATIONS

Dicuio et al, "Measurements of Urinary Bladder Volume: Comparison of Five Ultrasound Calculation Methods in Volunteers", Archivio Italiano Di Urologia E Andrologia, vol. 77, No. 1, 2005, pp. 60-62.

(Continued)

Primary Examiner — Long V Le
Assistant Examiner — Colin T Sakamoto (57) ABSTRACT The present invention provides a device and a method for monitoring the bladder volume of a subject. A device for monitoring the bladder volume of a subject comprises a sensor to be attached to a region on the exterior surface of the abdomen of the subject, the region corresponding to the bladder of the subject, the sensor being configured to obtain a sensor signal indicating the bladder volume of the subject; a controlling unit configured to generate a control action signal if it determines, based on the sensor signal, that the change of the bladder volume of the subject exceeds a predetermined amount; an ultrasound probe to be attached to the subject and configured to emit, in response to the control (Continued)

signal, an ultrasonic signal toward the bladder of the subject and receive echo signals from the bladder of the subject; a deriving unit configured to derive the bladder volume of the subject from the received echo signals. According to the device, long-time monitoring of the bladder volume of the subject may be achieved.

15 Claims, 3 Drawing Sheets

(51) Int. Cl.
*A61B 5/00* (2006.01)
*A61B 8/00* (2006.01)

(52) U.S. Cl.
CPC .......... *A61B 8/4494* (2013.01); *A61B 8/5223* (2013.01); *A61B 8/5276* (2013.01); *A61B 8/54* (2013.01); *A61B 8/56* (2013.01); *A61B 5/7221* (2013.01); *A61B 2560/0209* (2013.01); *A61B 2562/06* (2013.01)

(56) References Cited

U.S. PATENT DOCUMENTS

| | | |
|---|---|---|
| 2008/0139934 A1 | 6/2008 | McMorrow et al. |
| 2010/0160784 A1 | 6/2010 | Poland et al. |
| 2010/0160785 A1 | 6/2010 | Poland et al. |
| 2010/0312120 A1 | 12/2010 | Meier |
| 2011/0279683 A1* | 11/2011 | Yarmchuk .............. H04N 5/232 348/169 |
| 2012/0101389 A1 | 4/2012 | Tanabe |
| 2013/0003917 A1 | 1/2013 | Kim et al. |
| 2013/0303917 A1 | 11/2013 | Ona et al. |

FOREIGN PATENT DOCUMENTS

| | | |
|---|---|---|
| JP | 2003503104 A | 1/2003 |
| JP | 2009279435 A | 12/2009 |
| JP | 2010057541 A | 3/2010 |
| WO | 0100117 A2 | 1/2001 |
| WO | 2006023984 A1 | 3/2006 |
| WO | 2010020939 A2 | 2/2010 |
| WO | 2012078639 A1 | 6/2012 |
| WO | 2013133484 A1 | 9/2013 |

OTHER PUBLICATIONS

Niu et al, "Design of an Ultrasound Bladder Volume Measurement and Alarm Sytem", Chinese Journal of Scientific Instrument, 2011, vol. 32(8):1858-1863.
Mcube Technology Co., Ltd, Downloaded From www.mcubetech.co.kr on Feb. 14, 2017, 2 pages.
Verathon Bladderscan, Downloaded From http://veraton.com/products/bladderscan on Feb. 14, 2017, 4 pages.
Urinary Bladder, Downloaded From http://en.wikipedia.org/wiki/urinary_bladder, on Feb. 14, 2017, 6 pages.

* cited by examiner

DEVICE AND METHOD FOR MONITORING BLADDER VOLUME OF A SUBJECT

This application is the U.S. National Phase application under 35 U.S.C. §371 of International Application No. PCT/EP2015/051743, filed on Jan. 28, 2015, which claims the benefit of European Patent Application No. 14168412.6, filed May 15, 2014 and of International Application No. PCT/CN2014/071668, filed Jan. 28, 2014. These applications are hereby incorporated by reference herein.

FIELD OF THE INVENTION

The present invention generally relates to medical monitoring of a subject, e.g., a patient, especially monitoring of the bladder volume of the subject.

BACKGROUND OF THE INVENTION

The bladder is an organ that collects urine excreted by kidneys before disposal by urination. As urine accumulates in the bladder of a patient, increases the bladder volume of the patient and thus increases the internal pressure of the bladder. In response to the increased internal pressure of the bladder reaching a critical pressure level, the patient may feel the urge to urinate.

There are several conditions which may affect urination from the bladder of a patient. Bladder dysfunction, e.g., incontinence and urine retention, is one of them. Another condition is marrow nerve damage due to which a patient cannot respond to internal pressure of his/her bladder. Generally, such marrow nerve damage may be caused by trauma.

Several methods have been used for patients suffering from such conditions. One method is to implant a pressure sensor into the bladder of the patient and detect the moment at which the pressure of the bladder, indicated by the pressure sensor, reaches a critical pressure level. However, implantation of a pressure sensor is invasive and often very expensive. Another method is to measure the bladder volume of the patient non-invasively using ultrasound imaging. Several devices for automated portable bladder volume measurement have been developed based on ultrasound imaging techniques. However, the devices are designed for general checking in daily clinical practice and their battery can be used for several hours only, therefore, the devices are not suitable for long-time monitoring and warning.

U.S. Pat. No. 6,372,951 B1 discloses a disposable article to be fitted to a wearer. The disposable article preferably comprises a sensor operatively connected to the article. The article may comprise a monitoring system including a piezoelectric transducer that measures the volume of a fluid-filled cavity in the body, such as a bladder or rectum. When stimulated, the piezoelectric transducer sends an ultrasound pulse into the abdomen. The pulse may be sent out at any pre-defined or random interval.

SUMMARY OF THE INVENTION

Therefore, it would be desirable to provide a device and a method for achieving long-time monitoring of the bladder of a subject, e.g., a patient, in an automated and non-invasive manner.

According to the present invention, a sensor is attached to a region on the exterior surface of the abdomen of the patient and used for obtaining sensor signals indicating the bladder volume of the patient continually, the region corresponding to the bladder of the patient. For example, the sensor can be attached to a region on the skin of the subject or patient above the bladder volume. Ultrasound imaging of the bladder of a patient is triggered when, based on a sensor signal of the continually obtained sensor signals, it is determined in real time that the change of the bladder volume of the patient exceeds a predetermined amount, so as to perform the ultrasound imaging in a discrete mode. Therefore, the total monitoring time using ultrasound imaging may be prolonged, wherein the bladder volume generally increases as urine accumulates in the bladder of the subject as a dynamic process.

In addition, the sensor signal from the sensor attached to the region on the exterior surface of the abdomen of the subject corresponding to the bladder of the patient may coarsely indicate bladder volume and internal pressure of the bladder of the patient, therefore, by using it to trigger more accurate bladder volume measurement by ultrasound imaging of the patient, comparable monitoring of the bladder of the patient through continuous monitoring of the bladder using ultrasound imaging can be achieved. In one embodiment of the invention, the sensor may be a pressure sensor which may obtain a pressure signal indicating internal pressure of the bladder of the patient and thereby indirectly indicating the bladder volume of the subject. In another embodiment of the invention, the sensor may be a linear displacement sensor which may obtain a perimeter signal indicating the perimeter of the abdomen of the subject and indirectly indicating the bladder volume of the subject.

In one aspect, the present invention provides a device for monitoring bladder volume of a subject. The device comprises a sensor to be attached to a region on the exterior surface of the abdomen of the subject, the region corresponding to the bladder of the subject, the sensor being configured to obtain a sensor signal indicating the bladder volume of the subject; a controlling unit configured to generate a control signal if it determines that the change of the bladder volume of the subject exceeds a predetermined amount based on the sensor signal; an ultrasound probe to be attached to the subject and configured to emit, in response to the control signal, an ultrasonic signal toward the bladder of the subject and receive echo signals from the bladder of the subject; a deriving unit configured to derive the bladder volume of the subject from the received echo signals. The predetermined amount may be a constant in some embodiments and time-varied in other embodiments.

In one embodiment, the controlling unit is further configured to determine whether the derived bladder volume of the subject reaches a predefined threshold, and the device of the invention further comprises an alarm configured to give an alarm if the controlling unit determines that the derived bladder volume of the subject reaches the predefined threshold. Therefore, the device of the invention may be adapted for providing a warning when the bladder volume of the subject reaches a critical volume for urination.

In one embodiment, the device further comprises a low-pass filtering unit configured to apply low-pass filtering to the sensor signal, and the controlling unit determines whether the change of the bladder volume of the subject exceeds the predetermined amount based on the low-pass filtered sensor signal of the subject. According to the embodiment, artifacts such as those induced by respiration of the subject may be at least partially eliminated by means of said low-pass filtering, because respiration change is more frequent than bladder volume change.

As an alternative, the device further comprises one or more additional sensors to be attached to one or more additional regions on the exterior surface of the abdomen of the subject outside the region corresponding to the bladder of the subject and adapted to obtain one or more additional sensor signals, wherein the controlling unit determines whether the change of the bladder volume of the subject exceeds the predetermined amount based on the sensor signal and the one or more additional sensor signals. According to the embodiment, artifacts such as those induced by the subject's respiration may also be at least partially eliminated, because the one or more additional sensor signals obtained outside the bladder region are expected to represent mostly the artifacts rather than the change of the volume, whilst the sensor signal obtained within the bladder region is expected to represent a combination of the artifacts and the change of the bladder volume.

In one embodiment, the device further comprises a movement detecting unit configured to obtain movement data of the subject. The controlling unit is further configured to determine whether the variation rate of the movement data of the subject is less than a predetermined value and, if so, generate the control signal. In this way, artifacts due to movement of the subject may be at least partially eliminated.

Furthermore, the device may comprise a receiving unit for receiving a parameter value indicating the predefined threshold, wherein the controlling unit generates the predefined threshold based on the parameter value. Thus, the predefined threshold may be set to be different for different individual subjects by the device of the invention. In this way, the device can be adjusted to fit the various conditions or needs of different users. For example, the urge to void may be different for different users.

Moreover, the ultrasound probe of the invention may be improved in order to be attached to the subject in a fixed location for long-time monitoring and in order to derive the volume of the bladder of the subject.

In one embodiment, the ultrasound probe comprises an ultrasound transducer comprising two sets of ultrasound transducer elements configured in a cross shape or T shape, each set comprising one or more ultrasound transducer elements. In particular, the two sets of ultrasound transducer elements respectively form the two bars of the cross-shape or T-shape and are configured to emit ultrasonic signals toward the bladder of the subject in a set-by-set sequential manner.

In another embodiment, the ultrasound probe comprises two separate ultrasound transducers which are configured in a cross shape or T shape, each of which comprises one or more ultrasound transducer elements. In particular, the two ultrasound transducers respectively form the two bars of the cross-shape or T-shape and are configured in a cross-shape or T-shape sequentially emit ultrasonic signals toward the bladder of the subject.

In a further embodiment, the ultrasound probe comprises a capacity micro-machined ultrasound transducer (CMUT).

In another aspect, the present invention provides a method of monitoring the bladder volume of a subject. The method comprises a) obtaining a sensor signal indicating the bladder volume of the subject by means of a sensor to be attached to a region on the exterior surface of the abdomen of the subject, the region corresponding to the bladder of the subject; b) generating a control signal if it is determined that the change of the bladder volume of the subject exceeds a predetermined amount based on the sensor signal; c) in response to the control signal, emitting an ultrasonic signal toward the bladder of the subject and receiving echo signals from the bladder of the subject by an ultrasound probe; d) deriving the bladder volume of the subject from the received echo signals; e) determining whether the derived bladder volume of the subject reaches a predefined threshold; f) repeating the steps a)-e) if it is determined that the derived bladder volume of the subject does not reach the predefined threshold in step e).

In a further aspect, the present invention provides a computer program product which comprises computer program instructions which, when executed, enable the device of the invention to perform the method of the invention.

Various aspects and features of the disclosure are described in further detail below. And other objects and advantages of the present invention will become more apparent and will be easily understood with reference to the description made in combination with the accompanying drawings.

DESCRIPTION OF THE DRAWINGS

The present invention will be described and explained hereinafter in more detail in combination with embodiments and with reference to the drawings, wherein.

The same reference signs in the figures indicate similar or corresponding features and/or functionalities.

DETAILED DESCRIPTION

The present invention will be described with respect to particular embodiments and with reference to certain drawings, but the invention is not limited thereto but only by the claims. The drawings described are only schematic and are non-limiting. In the drawings, the size of some of the elements may be exaggerated and not drawn to scale for illustrative purposes.

Figure 1:
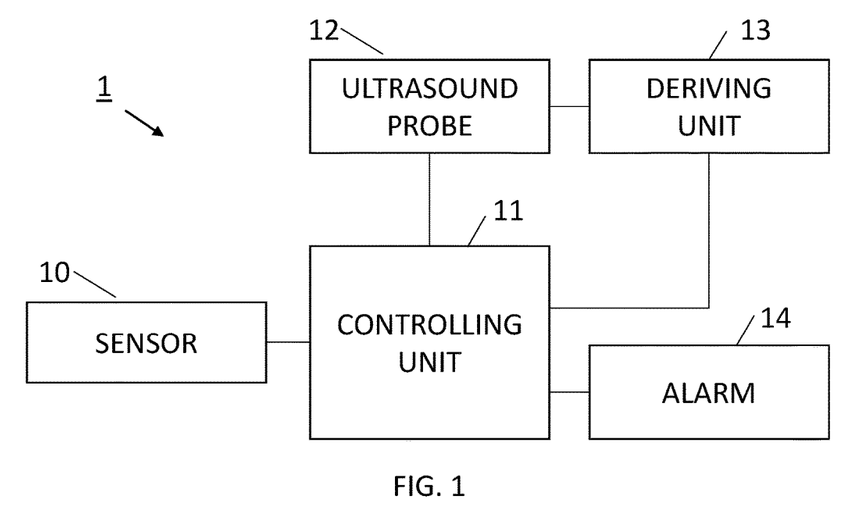
FIG. 1 is a schematic block diagram of a device 1 for monitoring the bladder volume of a subject according to one embodiment of the present invention.

FIG. 1 shows a device 1 for monitoring the bladder volume of a subject, e.g., a patient, according to one embodiment of the present invention. The device 1 comprises a sensor 10 which may be attached to a region on the exterior surface of the abdomen of the subject corresponding to the bladder of the subject and which obtains a sensor signal indicating the bladder volume of the subject; a controlling unit 11 which generates a control signal when it is determined that the change of the bladder volume of the subject exceeds a predetermined amount based on the sensor signal; an ultrasound probe 12 which is to be attached to the subject and which is configured to emit, in response to the control signal, an ultrasonic signal toward the bladder of the subject and which receives echo signals from the bladder of the subject; and a deriving unit 13 which derives the bladder volume of the subject from the received echo signals.

The sensor 10 is used for obtaining a sensor signal which may indirectly indicate the bladder volume of a subject. In one preferred embodiment, the sensor 10 may be a pressure sensor, e.g., a piezoelectric sensor, and the sensor signal is a pressure signal indicating internal pressure of the bladder of the subject. Since the volume of the bladder of the subject increases proportionally with the internal pressure of the bladder of the subject, the pressure signal may indirectly indicate the bladder volume of the subject.

However, the sensor 10 is not limited to a pressure sensor; any kind of other sensor which can generate a sensor signal directly or indirectly indicating the bladder volume of the subject may be used. Accordingly, the sensor signal is not limited to the pressure signal only; any kind of sensor signal which can directly or indirectly indicate the bladder volume of the subject may be used.

An example of an alternative sensor is a linear displacement sensor which is to be attached to the region on the exterior surface of the subject corresponding to the bladder of the subject. The linear displacement sensor can measure the perimeter of the abdomen of the subject. In this case, the sensor signal is a perimeter signal indicating the perimeter of the abdomen of the subject. Since the perimeter of the abdomen of the subject may increase as the bladder volume of the subject increases, the perimeter signal may reflect the bladder volume of the subject to some extent.

Certainly, the sensor signal may be a displacement signal obtained from the linear displacement sensor also. Such a displacement signal may indicate the change of the bladder volume of the subject.

The controlling unit 11 receives the sensor signal from the sensor 10 and determines whether the change of the bladder volume of the subject exceeds a predetermined amount based on the sensor signal. In one embodiment, the predetermined amount may be a value representing volume difference. In this case, a coarse value of the bladder volume can be derived from the sensor signal.

Preferably, the predetermined amount is an increment of the sensor signal, or a proportional increment, e.g., 5%, between the original sensor signal of the subject, e.g., the sensor signal obtained at the beginning of monitoring, and the current sensor signal of the subject. The controlling unit 11 determines whether the change of the sensor signal exceeds the predetermined amount directly. If the controlling unit 11 determines that the change of the sensor signal exceeds the predetermined amount, it generates the control signal.

The predetermined amount may be constant or the predetermined amount may be varied as the urine accumulates in the bladder of the subject. For example, the predetermined amount may be set to a large value after urination and reduces gradually until next urination. In this way, ultrasound imaging may be triggered more frequently when more urine accumulates in the bladder of the subject. Thus, the bladder volume may be derived more frequently as the next urination approaches and thus warning the patient about the next urination can be done in advance more accurately.

In addition, the predetermined amount may be varied for individual patients also.

It may be contemplated that the predetermined amount may be a pressure amount or a perimeter amount as long as it intimately correlates to the bladder volume change of the subject.

Certainly, it is possible that the sensor 10 obtains a sensor signal indicating the bladder volume change and the controlling unit 11 compares the sensor signal with the predetermined amount to determine whether the change of the bladder volume is sufficient to trigger the generation of the control signal.

In response to the control signal from the controlling unit 11, the ultrasound probe 12 transmits an ultrasonic signal toward the bladder of the subject and receives echo signals from the bladder of the subject. The ultrasonic signal comprises a series of ultrasonic pulses or ultrasonic waves. In order to attach the ultrasound probe to the subject in a fixed location for long-time monitoring and in order to change the transmission angle of the ultrasound probe to derive the volume of the bladder of the subject, the ultrasound probe may have the following configurations.

In one configuration, the ultrasound probe comprises an ultrasound transducer comprising two sets of ultrasound transducer elements configured in a cross shape or a T shape. The two sets of ultrasound transducer elements respective form the two bars of the cross shape or T shape. The two sets of ultrasound transducer elements are configured to emit ultrasonic signals toward the bladder of the subject in a set-by-set sequential manner. Each set of the ultrasound transducer elements may include one or more ultrasound transducer elements. In this way, the two sets of ultrasound transducer elements may be controlled by only one controller to sequentially emit the ultrasonic signals to the subject.

In another configuration, the ultrasound probe comprises two separate ultrasound transducers which are configured so as to respectively be the two bars of the cross-shape or T-shape. According to an embodiment of the present invention, the ultrasound transducers emit ultrasonic signals toward the bladder of the subject in a sequential manner. Each one of the ultrasound transducers may comprise one or more ultrasound transducer elements. This configuration may be simply achieved by two existing ultrasound transducers, and in this way the two ultrasound transducers can be controlled separately.

Such a configured ultrasound probe is light-weight and thin, and it is easy to change the transmission angle of the ultrasonic signal of the ultrasound probe so as to facilitate the deriving of the bladder volume of the subject.

In one preferred embodiment, the ultrasound probe comprises a capacity micro-machined ultrasound transducer (CMUT).

The deriving unit 13 receives the echo signals from the ultrasound probe 12, generates image data of the bladder of the subject and derives the bladder volume of the subject based on the image data of the bladder of the subject. The commonly used methods for deriving the bladder volume comprise the prolate ellipsoid method, double area method and double ellipsoid method. The derived bladder volume may be displayed on a display (not shown) for a user. In some embodiments, one or more 2D or 3D images can be further generated from the image data and displayed. In other embodiments, no ultrasound image is generated or displayed.

In one embodiment, the derived bladder volume may be transmitted to the controlling unit 11 which compares the derived bladder volume with a predefined threshold. If the derived bladder volume reaches or exceeds the predefined threshold, the controlling unit 11 triggers an alarm 14 to give an alarm to the user. The alarm may be a visual signal displayed on the display (not shown) or an audio signal.

Figure 2:
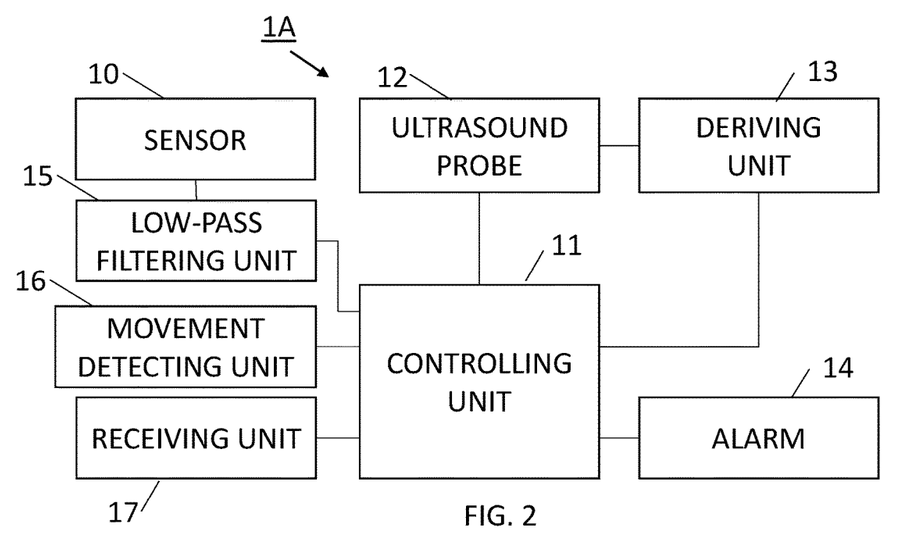
FIG. 2 is a schematic block diagram of a device 1A for monitoring the bladder volume of a subject according to another embodiment of the present invention.

The predefined threshold may be preset in the controlling unit 11. Alternatively, the predefined threshold may be received from the user via a receiving unit 17, as shown in FIG. 2. Preferably, the receiving unit 17 may receive a parameter value indicating the predefined threshold and the controlling unit 11 generates the predefined threshold based on the parameter value. In this case, the predefined threshold may be set based on individual subjects, more particularly, different urges to void of different individual patients. That is, the predefined threshold may be set to be different for different individual subjects.

In FIG. 2, a device 1A is illustrated. In one preferred embodiment, the device 1A further comprises a low-pass filtering unit 15 which is used to at least partially eliminate artifacts, induced by respiration of the subject, e.g., the patient, from the sensor signal, e.g., the pressure signal or the displacement signal. Compared with the artifact caused by the respiration of the subject, the sensor signal is a low-frequency signal due to the increase of the bladder volume of the subject. This is because, compared with breathing cycles, the change of the bladder volume is very slow because the accumulation process of urine in the bladder is a very slow process. In addition, since the breathing signal is a near-sine signal, the low-pass filtering unit 15 may be designed to separate the low-frequency signal, i.e., the sensor signal, due to the increase of the bladder volume of the subject, from the near-sine signal through spectral analysis of the sensor signal.

The low-pass filtering unit 15 receives the sensor signal, e.g., the pressure signal or the perimeter signal, from the sensor 10 and performs low-pass filtering on the sensor signal to at least partially eliminate the artifacts caused by the respiration of the subject. In this case, the controlling unit 11 determines whether the bladder volume change of the subject exceeds the predetermined amount based on the low-pass filtered sensor signal of the subject.

Instead of using the low-pass filtering unit 15, one or more additional sensors (not shown) may be attached to one or more additional regions on the exterior surface of the abdomen of the subject outside the region corresponding to the bladder of the subject. Since the one or more additional sensors are not attached to the region corresponding to the bladder of the subject, i.e., the bladder region, one or more additional sensor signals obtained by the one or more additional sensors substantially do not include the sensor signal caused by the increase of the bladder volume of the subject, but include the artifacts such as those induced by the respiration of the subject. In this case, the controlling unit 11 receives the one or more additional sensor signals from the one or more additional sensors also and determines whether the bladder volume change of the subject exceeds the predetermined amount based on the sensor signal and the one or more additional sensor signals. In the case of one additional sensor, the controlling unit 11 determines whether the bladder volume change of the subject exceeds the predetermined amount based on a difference between the sensor signal and the additional sensor signal. In the case of a plurality of additional sensors, a plurality of differences between the sensor signal and individual additional sensor signals of a plurality of additional sensor signals from the plurality of additional sensors may be averaged and the controlling unit 11 determines whether the bladder volume change of the subject exceeds the predetermined amount based on the averaged difference. In this case, it is preferred that the sensor 10 and the additional sensors are the same kind of sensor. In one embodiment, both of them are pressure sensors. In another embodiment, both of them are linear displacement sensors.

In another preferred embodiment, the device 1A may further comprise a movement detecting unit 16, e.g., an accelerometer, which collects movement data of the subject. In this embodiment, the controlling unit 11 determines whether the variation rate of the movement data of the subject is less than a predetermined value, and generates the control signal if it determines that the variation rate of the movement data of the subject is less than the predetermined value. In particular, the controlling unit 11 receives the movement data of the subject from the movement detecting unit 16, determines the variation rate of the movement data of the subject, e.g., by determining a derivative of the movement data, compares the variation rate with the predetermined value, e.g., input by a user or a patient, and generates the control signal when the variation rate of the movement data of the subject is less than the predetermined value.

In this case, the control signal is generated by taking both the sensor signal and the variation rate of the movement data of the subject into consideration. Therefore, artifacts due to movement of the subject may be at least partially eliminated and thus a more accurate bladder volume may be derived.

Although the device 1 of the invention is described with respect to a sensor 10, a controlling unit 11, an ultrasound probe 12, a deriving unit 13 and an alarm 14, as shown in FIG. 1, and the device 1A of the invention is described with respect to a sensor 10, a controlling unit 11, an ultrasound probe 12, a deriving unit 13, an alarm 14, a low-pass filtering unit 15, a movement detecting unit 16 and a receiving unit 17, as shown in FIG. 2, it will be understood that the device of the invention is not limited to the configurations described above. One or more components of the device may be omitted or integrated into one component to perform the same function. Or, one or more components of the device may be omitted directly to omit their function without affecting the implementation of the invention. For example, for a patient who cannot move, the movement detecting unit 16 may be omitted.

Furthermore, it may be determined that the controlling unit 11, the deriving unit 13, and the low-pass filtering unit 15 of the device of the invention may be achieved by any one of software, hardware, firmware or a combination thereof. In particular, they may be achieved not only by computer programs for performing corresponding functions but also by various entity devices, such as application-specific integrated circuits (ASIC), digital signal processors (DLP), programmable logic devices (PLD), field-programmable gate arrays (FPGA), and CPU. More particularly, they may be implemented as part of a handheld computer or laptop for home monitoring purpose or as part of a hospital central workstation for hospital monitoring purpose.

It may be anticipated that the device of the invention may be used not only for a single evaluation of the bladder volume of the subject for initial screening but also for long-time serial monitoring of the bladder volume of the subject. In the case of long-time monitoring of the bladder volume of the subject, the sensor 10 and the ultrasound probe 12 are to be attached to the subject at a fixed location, and other components of the device may be integrated into a handheld device or a wearable device, e.g., a handheld or wearable processor, for home monitoring purpose and into a bedside monitoring device or a workstation for hospital monitoring purpose. The sensor 10 obtains sensor signals continually. The controlling unit 11 receives the sensor signals and determines whether the bladder volume change of the subject exceeds a predetermined amount based on each of the sensor signals. The controlling unit 11 generates the controlling signal when it is determined that the bladder volume change of the subject exceeds a predetermined amount based on the sensor signals. Similarly, the low-pass filtering unit 15 and the movement detecting unit 16 may also be adapted for long-time monitoring.

It may also be anticipated that the signals or data may be transferred between the components of the device of the invention in wired or wireless manner.

It may be contemplated that the device of the invention may be achieved by means of a sensor to be attached to the subject, any kind of ultrasound imaging system, and one of a handheld computer or laptop and a hospital central workstation.

It may also be contemplated that the device of the invention may comprise a plurality of sensors 10, a plurality of ultrasound probes 12, and optionally a plurality of movement detecting units 16, which are to be used to monitor a plurality of subjects, e.g., patients. Each of the plurality of subjects is provided with a sensor 10, an ultrasound probe 12, and optionally a movement detecting unit 16. According to an embodiment of the present invention, the controlling unit 11, the deriving unit 13, the alarm 14 as well as the low-pass filtering 15 may be incorporated into a central unit such as a workstation. The central unit is configured to communicate with each sensor 10, each ultrasound probe 12 and each movement detecting unit 16 in wired or wireless manner. In an embodiment, each of the plurality of subjects may be further provided with a communicating unit, which is connected to the sensor 10, the ultrasound probe 12 and the movement detecting unit 16 provided to that subject and is configured to relay the communication with the center unit.

It may be further contemplated that any one of a predetermined amount, a predefined threshold and a predetermined value may be preset, before delivery of the device to a patient, or received from a user via a receiving unit 17.

Figure 3:
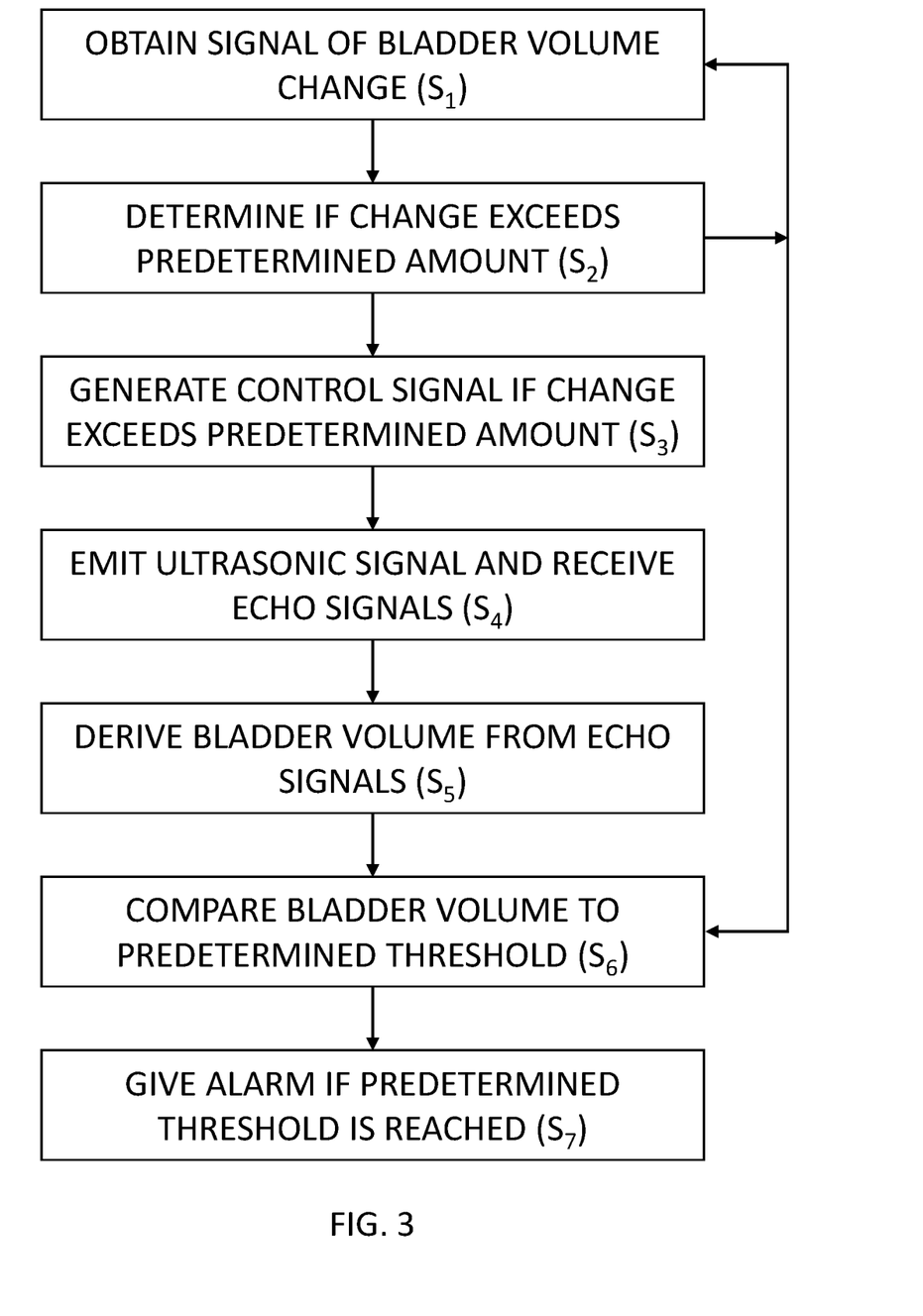
FIG. 3 is a flowchart of a method for monitoring the bladder volume of a subject according to one embodiment of the present invention.

FIG. 3 shows a flowchart of a method of monitoring the bladder volume of a subject according to one embodiment of the present invention. In step $S_1$, a sensor signal indicating the bladder volume change of the subject is obtained by means of a sensor 10 attached to a region on the exterior surface of the abdomen of the subject, the region corresponding to the bladder of the subject. In one embodiment, the sensor signal may be a pressure signal indicating internal pressure of the bladder of the subject. In a preferred embodiment, one or more additional sensor signals may be obtained from one or more additional regions on the exterior surface of the abdomen of the subject outside the region corresponding to the bladder of the subject.

In step $S_2$, it is determined whether the change of the bladder volume of the subject exceeds a predetermined amount based on the sensor signal and an additional sensor signal, if any, of the subject.

In particular, if no additional sensor signal is obtained, by determining that the change of the sensor signal has reached a predefined criterion it may be determined that the change of the bladder volume of the subject exceeds the predetermined amount. In the case where one additional sensor signal is obtained, it may be determined whether the change of the bladder volume of the subject exceeds the predetermined amount based on the sensor signal and the additional sensor signal, more particularly, based on the difference between the sensor signal and the additional sensor signal. In the case where a plurality of additional sensor signals are obtained, as described above, the averaged difference between the sensor signal and an individual additional sensor signal of a plurality of additional sensor signals may be used.

If it is determined that the change of the bladder volume of the subject exceeds the predetermined amount, a control signal is generated in step $S_3$. Otherwise, no control signal is generated and the process returns to step $S_1$.

In step $S_4$, in response to the control signal, an ultrasound probe emits an ultrasonic signal toward the bladder of the subject and receives echo signals from the bladder of the subject.

In step $S_5$, the bladder volume of the subject is derived from the received echo signals. In particular, a 2D/3D image is generated from the received echo signals and the bladder volume of the subject is derived from the image using algorithms known in the art, as described above.

In step $S_6$, the derived bladder volume of the subject is compared with a predefined threshold. If it is determined that the derived bladder volume of the subject reaches the predefined threshold, an alarm is given in step $S_7$. Otherwise, no alarm is given and the process returns to step $S_1$.

Figure 4:
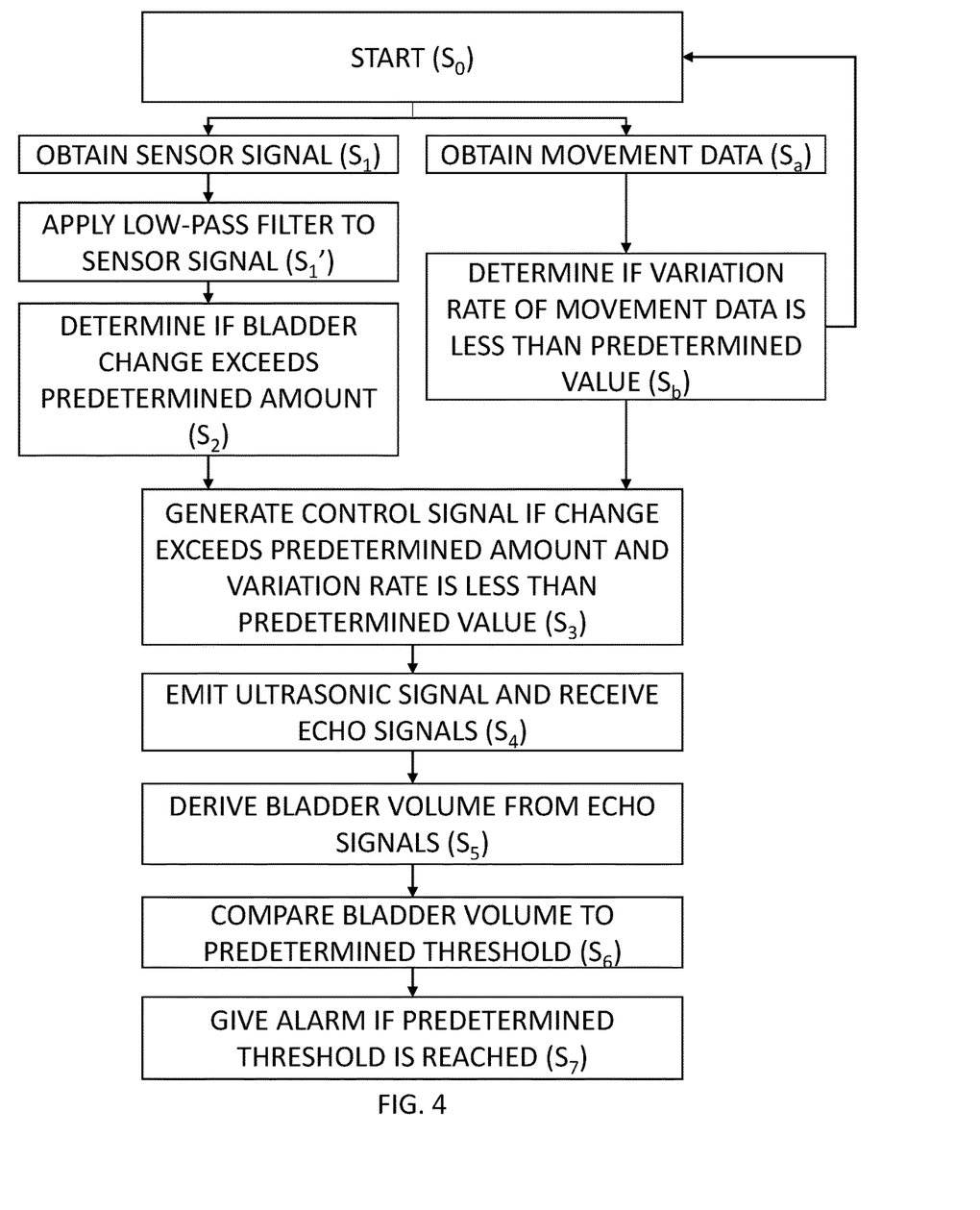
FIG. 4 is a flowchart of a method for monitoring the bladder volume of a subject according to another embodiment of the present invention.

FIG. 4 shows a flowchart of a method of monitoring the bladder volume of a subject according to another embodiment of the present invention. Most of the steps shown in FIG. 4 are the same as those in FIG. 3. The method shown in FIG. 4 is different from that shown in FIG. 3 in that the method shown in FIG. 4 comprises steps $S_0$, $S_1'$, $S_a$ and $S_b$. The step $S_0$ indicates the start of the method of the invention. After the start of the method of the invention in step $S_0$, steps $S_1$ and $S_a$ are performed.

In step $S_1'$, the sensor signal obtained in step $S_1$ is low-pass filtered to at least partially eliminate artifacts caused by respiration of a subject. In this case, in step $S_2$, whether the change of the bladder volume of the subject exceeds a predetermined amount is determined based on the low-pass filtered sensor signal, and if it is determined that the change of the bladder volume of the subject fails to exceed a predetermined amount, the process returns to step $S_0$ to restart the method of the invention.

In step $S_a$, movement data of the subject is obtained. In step $S_b$, it is determined whether the variation rate of the movement data of the subject is less than a predetermined value. If it is determined that the variation rate of the movement data of the subject is less than the predetermined value, the process proceeds to step $S_3$. Otherwise, it returns to step $S_0$ to restart the method of the invention.

According to the method of the embodiment, in step $S_3$, a control signal is generated when the following two requirements are met: (1) it is determined that the change of the bladder volume of the subject exceeds the predetermined amount based on the sensor signal and (2) the variation rate of the movement data of the subject is less than the predetermined value.

Although the methods of the invention are described with respect to the steps shown in FIGS. 3 and 4, it may be understood that some of the steps may be omitted to omit their function without affecting the implementation of the invention. For example, for a patient who cannot move, steps $S_a$ and $S_b$ may be omitted. It may also be understood that some of the steps may be combined into one step to fulfill the same function.

Please note that the device according to the present invention should not be limited to the device mentioned above. It will be apparent to those skilled in the art that the various aspects of the invention claimed may be practiced in other examples that depart from these specific details.

Furthermore, the mere fact that certain measures are recited in mutually different dependent claims does not indicate that a combination of these measures cannot be used to advantage.

It should be noted that the above-mentioned embodiments illustrate rather than limit the invention and that those skilled in the art would be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the product claims enumerating several units, several of these units can be embodied by one and the same item of software and/or hardware. The usage of the words first, second and third, et cetera, does not indicate any ordering. These words are to be interpreted as names.

The invention claimed is:

1. A device for monitoring a subject's bladder volume, the device comprising:
   a sensor configured to:
      attach to an exterior surface of the subject's abdomen at a region corresponding to the subject's bladder, and obtain a sensor signal indicative of the subject's bladder volume;
   an ultrasound probe configured to:
      attach to the subject;
      emit an ultrasonic signal; and
      receive echo signals;
   a controlling unit configured to;
      determine, based on the sensor signal, if a change in the subject's bladder volume exceeds a predetermined amount; and
      if the change of the bladder volume of the subject exceeds the predetermined amount, control the ultrasound probe to emit an ultrasonic signal toward the subject's bladder and receive echo signals from the subject's bladder;
   a deriving unit configured to derive the subject's bladder volume from the received echo signals from the subject's bladder.

2. The device of claim 1, wherein the device further comprises an alarm, and wherein the controlling unit is further configured to;
   determine whether the derived bladder volume of the subject reaches a predefined threshold,
   control the alarm to alert a user that the derived bladder volume reached the predefined threshold if the controlling unit determines that the derived bladder volume of the subject reaches the predefined threshold.

3. The device of claim 1, wherein the device further comprises a low-pass filtering unit configured to apply low-pass filtering to the sensor signal,
   wherein the controlling unit is configured to determine, based on the sensor signal, if the change the subject's bladder volume exceeds the predetermined amount by determining based on the low-pass filtered sensor signal whether a change of the subject's bladder volume exceeds the predetermined amount.

4. The device of claim 1, further comprises one or more additional sensors configured to:
   attach to the exterior surface of the subject's abdomen at one or more additional regions outside the region corresponding to the subject's bladder; and
   obtain one or more additional sensor signals, wherein the controlling unit is configured to determine, based on the sensor signal, if the change in the subject's bladder volume exceeds the predetermined amount by determining based on the sensor signal and the one or more additional sensor signals determines whether a change of the subject's bladder volume exceeds the predetermined amount.

5. The device of claim 1, further comprising:
   a movement detecting unit configured to obtain movement data of the subject;
   wherein the controlling unit is further configured to;
   determine whether a variation rate of the movement data of the subject is less than a predetermined value, and
   if the variation rate of the movement data of the subject is less than the predetermined value, control the ultrasound probe to emit the ultrasonic signal towards the subject's bladder and receive the echo signals from the subject's bladder.

6. The device of claim 2, further comprising:
   a receiving unit for receiving a parameter value indicating the predefined threshold,
   wherein the controlling unit is configured to generate the predefined threshold based on the parameter value.

7. The device of claim 1, wherein the ultrasound probe comprises an ultrasound transducer comprising two sets of ultrasound transducer elements configured in a cross shape or T shape, each set comprising one or more ultrasound transducer elements.

8. The device of claim 1, wherein the ultrasound probe comprises two separate ultrasound transducers which are configured in a cross shape or T shape, each transducer comprising one or more ultrasound transducer elements.

9. The device of claim 1, wherein the sensor comprises a piezoelectric sensor configured to obtain a pressure signal indicative of internal pressure from the subject's bladder, and the sensor signal comprises the pressure signal.

10. The device of claim 1, wherein the sensor comprises a linear displacement sensor configured to obtain a perimeter signal indicative of a perimeter of the subject's abdomen, and the sensor signal comprises the perimeter signal.

11. A method of monitoring a subject's bladder volume, the method comprising;
   a) obtaining a sensor signal indicating the subject's bladder volume by means of a sensor when the sensor is attached to an exterior surface of the subject's abdomen at a region corresponding to the subject's bladder;
   b) determining, based on the sensor signal, whether a change in the subject's bladder volume exceeds a predetermined amount based on the sensor signal;
   c) if the change of the bladder volume of the subject exceeds a predetermined amount, then emitting an ultrasonic signal toward the subject's bladder and receiving echo signals from the subject's bladder by means of an ultrasound probe;
   d) deriving the subject's bladder volume of the subject from the received echo signals;
   e) determining whether the derived bladder volume of the subject reaches a predefined threshold;
   f) if it is determined that the derived bladder volume of the subject does not reach the predefined threshold in the step e), then repeating steps a)-e).

12. The method of claim 11, further comprising alerting a user if the derived bladder volume of the subject reaches the predefined threshold in the step e).

13. The method of claim 12, further comprising:
   applying low-pass filtering to the sensor signal, wherein the determining, based on the sensor signal, whether a change in the subject's bladder volume exceeds a predetermined amount based on the sensor signal in step b) comprises determining, based on the low-pass filtered sensor signal, that the change of the bladder volume of the subject exceeds the predetermined amount.

14. The method of claim 11, further comprising:
   obtaining movement data of the subject; and
   determining whether a variation rate of the movement data of the subject is less than a predetermined value, wherein step c) further comprises:
   if the variation rate of the movement data of the subject is less than a predetermined value, emitting an ultrasonic signal toward the subject's bladder and receiving echo signals from the subject's bladder by means of the ultrasound probe.

15. A non-transitory computer readable medium having stored therein computer program instructions, which, when executed by a control unit, cause the control unit to:
a) receive a sensor signal indicating a subject's bladder volume from a sensor attached to an exterior surface of the subject's abdomen at a region corresponding to the subject's bladder;
b) determine, based on the sensor signal signal, whether a change in the subject's bladder volume exceeds a predetermined amount based on the sensor signal;
c) if the change of the bladder volume of the subject exceeds the predetermined amount, then control an ultrasound probe to emit an ultrasonic signal toward the subject's bladder and receive echo signals from the subject's bladder;
d) derive the bladder volume of the subject from the received echo signals;
e) determine whether the derived bladder volume of the subject reaches a predefined threshold;
f) if it determined that the derived bladder volume of the subject does not reach the predefined threshold in step e), then repeat steps a)-e).

* * * * *